United States Patent [19]

Bulkowski

[11] Patent Number: 4,545,937

[45] Date of Patent: Oct. 8, 1985

[54] BINUCLEATING LIGAND-METAL COMPLEXES AS OXIDATION CATALYSTS

[75] Inventor: John E. Bulkowski, Newark, Del.

[73] Assignee: University of Delaware, Newark, Del.

[21] Appl. No.: 659,396

[22] Filed: Oct. 10, 1984

Related U.S. Application Data

[63] Continuation-in-part of Ser. No. 485,764, Apr. 18, 1983, abandoned.

[51] Int. Cl.[4] .................. C07C 50/00; C07C 37/58
[52] U.S. Cl. .................. 260/396 R; 260/239 R; 260/239 BC; 568/763; 568/771
[58] Field of Search ........ 260/396 R, 239 BC, 239 R; 568/771, 763, 7

[56] References Cited

U.S. PATENT DOCUMENTS

| | | | |
|---|---|---|---|
| 3,794,668 | 2/1974 | Larking | 568/771 |
| 3,796,732 | 3/1974 | Brenner | 260/396 R |
| 3,987,068 | 10/1976 | Reilly | 260/396 R |
| 4,250,335 | 2/1981 | Bitter et al. | 568/771 |
| 4,478,752 | 10/1984 | Hsu et al. | 260/396 R |

FOREIGN PATENT DOCUMENTS 51-75030 6/1976 Japan.

OTHER PUBLICATIONS

Martell, "Acc. Chem. Res." (1982), vol. 15, pp. 155–162, Martin et al., reprint "J. Amer. Chem. Soc." vol. 104, p. 1434–(1982).

Martin et al., reprint "J. Organic Chem." vol. 47, pp. 412–415, (1982).

Demmin et al., "J. Ame. Chem. Soc." vol. 103, (1982) pp. 5795–5804.

Nelson Inorganic Chimica Acta" vol. 62, (1982), pp. 39–50.

Primary Examiner—Werren B. Lone

[57] ABSTRACT

There is taught a class of homogeneous oxidation catalysts characterized by the presence therein of two chelated cations of Cu(I) in each molecule.

8 Claims, 3 Drawing Figures $a = w = 2\text{-}5$
$b = x = 2$
$c = y = 1$
$d = z = 2$ $a = w = 4\text{-}5$
$b = x = 2$
$c = y = 0$
$d = z = 2$

BINUCLEATING LIGAND-METAL COMPLEXES AS OXIDATION CATALYSTS

This application is a continuation-in-part of application Ser. No. 485,764 filed 4/18/83 now abandoned.

BACKGROUND OF THE INVENTION

1. Field of the Invention

This invention pertains to catalysts comprising two cations coordinated within a single ligand molecule. Such catalysts catalyze the oxidation of phenols selectively at the ortho position with molecular oxygen under mild conditions.

2. Description of the Prior Art

Organic structures chelating two metal cations have received considerable attention in the past because of their ability, particularly those containing cobalt, to bind oxygen reversibly in the form of a dioxygen bridge between the cations. Martell in Accts. Chem. Res. 15 155 (1982) reviewed the art and reported the oxygenation and equilibrium quotients of some binuclear cobalt complexes comprising two diethylenetriamine chelating centers doubly bridged to form macrocycles.

In various forms, copper catalysts, to which the instant invention particularly pertains, have long been known to catalyze numerous reactions. Reilly in U.S. Pat. No. 3,987,068 reviewed the art of copper complex catalyzed oxidation of phenols and their derivatives, and taught the catalyzed oxidation with dioxygen of substituted and unsubstituted phenols and 1-naphthols at the 4-position. Reilly taught catalysts comprising Cu(I) and Cu(II) salts in complexing nitrile solution such as acetonitrile under substantial oxygen pressure at temperatures to 100° C.

At least two natural proteins appear to contain proximate copper atoms which seem to participate in unique reactions with dioxygen. One such protein, hemocyanin, reversibly binds dioxygen while another, tyrosinase, activates dioxygen whereby to catalyze the oxidation of organic substrates under mild conditions. The subject has been reviewed by Solomon in Copper Proteins (T. G. Spiro, editor) John Wiley & Sons, New York, N.Y. 2 Chpt. 3 (1981).

It is an object of this invention to provide proximate metal cation complexes which catalyze the oxidation of substrates under mild conditions in a manner analogous to that of the above-mentioned metalloproteins. A number of art complexes containing two metal cations in a single synthetic organic ligand are reported in the art: the so-called "ear muffs" of Bulkowski et al, J. Chem. Soc. Chem. Commun. 498 (1977); binucleating macrocycles of Couglin et al J. Am. Chem. Soc. 102 7616 (1980), Couglin et al J. Am. Chem. Soc. 101 265 (1979), Agnus et al, J. Am. Chem. Soc. 101 3381 (1979); Schiff bases reviewed by Groh, Isr. J. Chem. 15 277 L (1976/77) and taught by Grzybowski et al, Inorg. Chem. 19 2604 (1980), Gagne et al, J. Am. Chem. Soc. 101 6917 (1979), Fenton et al, J. Am. Chem. Soc. 100 1931 (1978), and Nelson, Inorg. Chim. Acta 62 39 (1982); so-called "wishbones" of Karlin et al, J. Chem. Soc. Chem. Comm. 881 (1981) Martell, Acc. Chem. Res. 15 155 (1982) as mentioned earlier, McKee et al, J. Am. Chem. Soc. 103 7000 (1981); cyptands of Lehn, IUPAC, Frontiers of Chemistry, Ed. K. J. Laidler, Pergamon Press 265 (1982); and open face macrocycles of Martin et al, J. Am. Chem. Soc. 104 1434 (1982).

Pasquali et al in Inorg. Chem. 17 1684 (1978) reported a mononuclear Cu(I) carbon monoxide complex of diethylenetriamine. Di Cu(I) macrocyclic complexes are not reported.

SUMMARY OF THE INVENTION

A catalyst useful for catalyzing dioxygen oxidative attack at a position ortho to a phenolic hydroxyl group under mild conditions, said catalyst comprising two proximate cations of Cu(I), each cation coordinated within a chelating center derived from ethylenediamine, diethylenetriamine, propylenediamine, and dipropylenetriamine, said centers being joined by two bridges selected from the group consisting of —$CH_2CH_2OCH_2CH_2$— and alkylene radicals containing 2 to 5 carbon atoms in the main chain, said bridges connecting terminal nitrogen atoms of said amines whereby to form a macrocycle ligand comprising said chelating centers, with the proviso that when at least one of the chelating centers is derived from ethylenediamine, the alkylene bridge radical, if present, contains at least 4 carbon atoms in the main chain.

DESCRIPTION OF THE PREFERRED EMBODIMENTS

Figure 1:
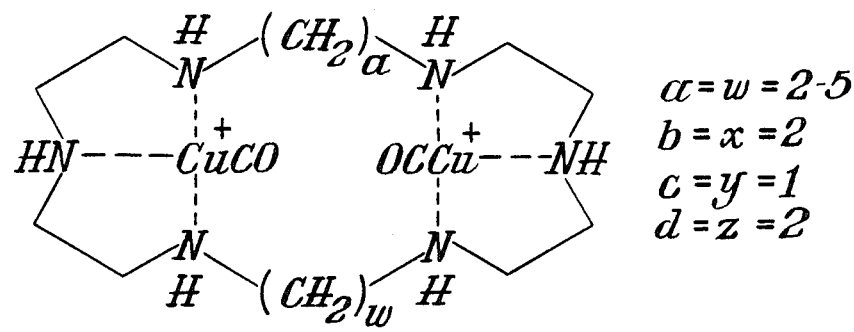
FIG. 1 is a schematic drawing representing the preferred catalyst of the invention comprising two diethylenetriamine chelating centers and FIG. 2 represents a less preferred catalyst comprising two ethylenediamine chelating centers. The accompanying equations show the corresponding values of subscripts in a general formula for ligands, as explained infra.

The catalysts of the invention comprise two proximate metal cations within a macrocyclic ligand comprising two chelating centers, each center chelating one of the cations. The ligands place two chelated metal cations of Cu(I) at a distance one from the other such that, on exposure to oxygen, dioxygen is bound between the cations as has been observed in the art in analogous compounds.

The ligands of the invention also permit access to the chelated cations of a substrate to be oxidized; i.e., the ligand is so selected as to permit, it is believed, the binding of a substrate, such as phenol, to the catalyst.

Suitable ligands for meeting these requirements are found, for example, among heteromacrocyclic compounds, many of which are known. Such macrocycles comprise two chelating centers each containing two or three trivalent nitrogen donor atoms. The nitrogen donor atoms of the chelating centers are normally separated from each other by two or three methylene groups. Thus the chelating centers, can be said to be derived from ethylenediamine, diethylenetriamine, propylenediamine, and dipropylenetriamine. Combinations such as ethylenepropylenetriamine are also operable and the two centers need not be the same.

The centers are joined by two bridges attached at the terminal nitrogen atoms of the chelating centers to form macrocycles of 16 to 28 members, preferably 20 to 24. The bridges, perferably alkylene radicals, each containing two to five methylene groups, need not be the same and are selected to meet the criterian that the chelated cations be not more than about 7 Å apart, as determined by a molecular model.

Ligands containing unsubstituted bridges, selected according to the above criteria, are operable. Substituted bridges, providing the substituents are not overly bulky, are generally operable. However, bulky substituents may sterically interfere with the binding of a substrate. The molecule designer is advised, therefore, to examine the molecular model of the ligand with this in mind before proceeding to synthesis. Similarly, the internitrogen methylene groups may be branched or substituted under the same constraints. For particular applications it may be useful to modify the physical properties of the catalysts, for example their solubility, by substitution. Catalyst mixtures are also operable.

The macrocyclic ligands in many cases are known compounds. They are readily prepared by the methods, or obvious modification thereof, of those taught by the art, for example, by Martin et al in J. Org. Chem 1982 47, 415 and by Lehn et al in J. Amer. Chem. Soc. 1977 99, 6766.

Some ligands containing nonalkylene bridges are also operable. For example, a $-CH_2CH_2OCH_2CH_2-$ group can replace one or both of the preferred alkylene bridges. A macrocyclic ligand having two such bridges was taught by Lehn et al supra and the corresponding di-Cu(II) chelate was prepared by Caughlin et al supra. The latter compound is not known to be an oxidation catalyst although a dioxygen bridge between Co(II) cations is reported by Martell supra. The novel di-Cu(I) chelate is expected to be operable as an oxidation catalyst according to this invention.

The cations may also be coordinated with so-called soft ligands such as CO which stabilize the lower oxidation state. They are released in the invention process.

The coodination geometry about the cations in the invention catalysts is thought to be similar to that found by x-ray crystallography by Pasquali et al in their monocopper complexes.

A number of suitable macrocyclic ligands can be summarized by the general formula:

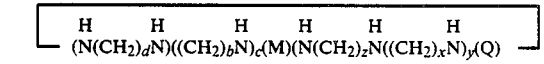

wherein
- a=2-5
- b=2 or 3
- c=0 or 1
- d=2 or 3
- w=2-5
- x=2 or 3
- y=0 or 1
- z=2 or 4;

with the proviso that when c=0, a≧4.

Preferred ligands, and those illustrated in examples, are those wherein
- a=w=5
- b=x=2
- c=y=1
- d=z=2 and
- a=w=3
- b=x=2
- c=y=1
- d=z=2

Figure 2:
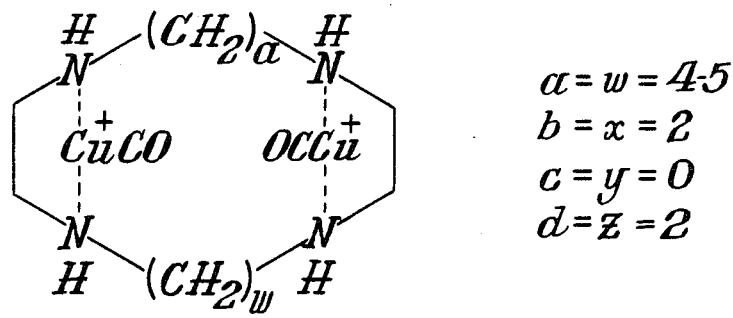

FIGS. 1 and 2 illustrate structures of CO-containing catalysts of the invention wherein each ligand comprises two chelating centers derived, in the former case from diethylenetriamine and, in the latter case, ethylenediamine. The former macrocycle is 1,4,7,13,16,19-hexaazacyclotetracosane and the latter is 1,4,10,13 tetraazacyclooctadecane. Shown on the drawings are the corresponding subscript values pertaining to the general macrocycle ligand formula supra. As shown in the drawings, two coordination sites are occupied by carbon monoxide. Anions are generally selected for reasons such as ease of isolation in preparing the catalyst. Anions are not shown in drawings.

The preferred ligands comprise two diethylenetriamine chelating centers joined by alkylene bridges of three, four, and five methylene groups.

The macrocycle ligand of Lehn et al supra belongs to a group of useful ligands comprising nonalkylene bridges. The group can be summarized by the above general formula with slight modification of the bridges designation, as follows:

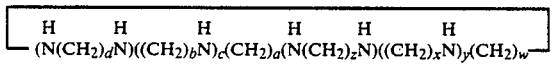

wherein M and Q are bridges in which one or both are $-CH_2CH_2OCH_2CH_2-$. If only one bridge is $-CH_2CH_2OCH_2CH_2-$, the other is an alkylene group containing two to five carbon atoms. In the macrocycle ligand of Lehn et al M=Q=$-CH_2CH_2OCH_2CH_2-$, b=x=2, c=y=1, and d=z=2.

Operability of the invention catalysts requires a lower oxidation state in the cation. Catalyst containing the cation in a lower oxidation state can be prepared by beginning the synthesis with the cation in that state, or the cation can be reduced in the finished compounds using a reductant such as a borohydride or ascorbic acid. In some cases it appears that the substrate itself is capable of reducing the cation to the lower oxidation state.

It appears that the combination of macrocycle ligands, cations and optionally soft ligands, selected and assembled as described, provide:

(a) an interatomic distance between the cations not greater than about 7 Å;
(b) a stable orientation of the cations such that two coordination sites, one on each cation, are generally oriented toward each other; and cis thereto
(c) two further sites, one on each cation, said sites being sterically capable of binding a substrate; and
(d) the sites of (b) and (c) being formally vacant or occupied by readily displaced entities.

Figure 3:
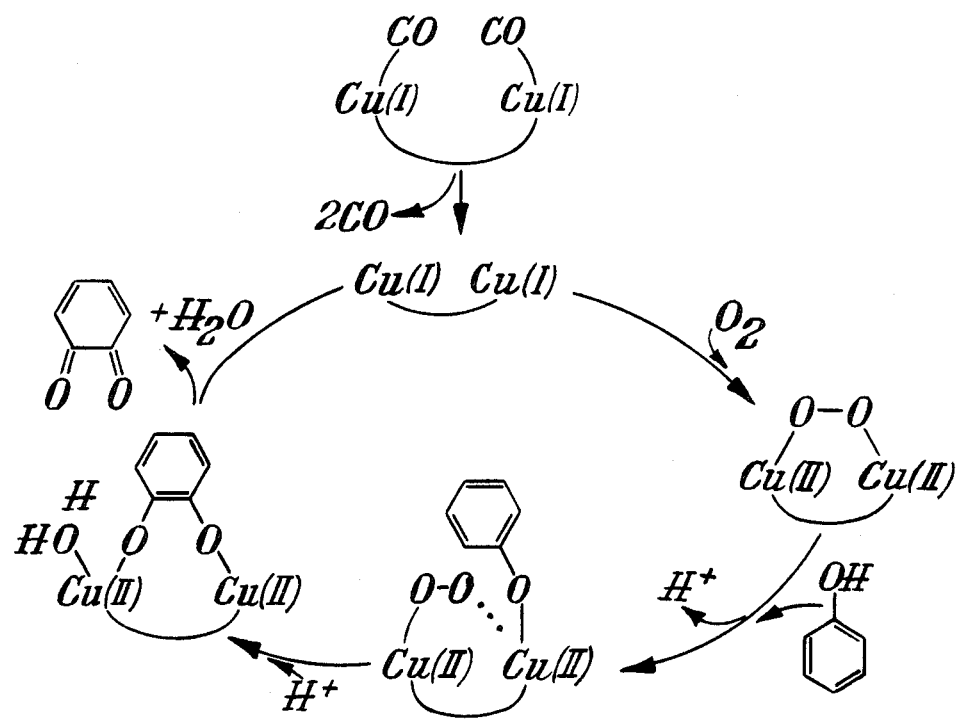
FIG. 3 shows a hypothetical reaction sequence for the catalyzed conversion of phenol to o-benzoquinone according to the invention.

FIG. 3 shows a hypothetical reaction sequence resulting in the oxidation of a phenol substrate to o-benzoquinone, according to the invention. The catalyst comprises two Cu(I) cations, as is preferred, and two readily displaced soft ligand carbon monoxide molecules coordinated thereto. They are contained within a ligand structure as described supra, which is here represented as an arc.

It will be noted that CO is released early in the sequence and dioxygen forms a bridge between the cations. Phenol is then bound to the cation at a site adjacent to the dioxygen-cation bond. The consequent close proximity of the dioxygen to the ortho position directs attack to that position. The intermediate thus formed breaks down to yield the product o-benzoquinone, water and catechol, not shown, by protonation of the intermediate.

EXAMPLES 1 & 2

Preparation and Characterization of Invention Catalysts

General Procedure

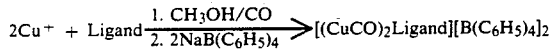

Finely divided cuprous iodide was suspended in abs. methanol (20 ml) under carbon monoxide at atmospheric pressure. During about 15 minutes a solution of ligand in abs. methanol (10 ml) was decanted from anhyd. $CaSO_4$ and added to the stirred suspension. After about 30 minutes the mixture was filtered in the absence of air and sodium tetraphenylborate was added to the filtrate. The catalyst precipitated as a white solid which was filtered, washed with methanol, and dried, first in a stream of carbon monoxide and then under vacuum. Other precipitants such as hexfluorophosphate and tetrafluoroborate may be employed.

EXAMPLE 1

Ligand: 1,4,7,13,16,19-hexaazacyclotetracosane

The yield of the invention catalyst, isolated as the colorless bis-tetraphenylborate complex, was 47% using 55 mg (0.289 mmole) CuI, 50 mg (0.146 mmole) ligand, and 100 mg (0.292 mmole) sodium tetraphenylborate.

Analysis calculated for $C_{68}H_{82}N_6O_2B_2Cu_2$: C, 70.16; H, 7.10; N, 7.22. Found: C, 69.02; H, 6.46; N, 7.23%. Characteristic IR absorption bands were observed at 3305 (m) and 3250 (m) for ligand NH; 2085 (s) for CO; and 710 (s) and 740 (s) $cm^{-1}$ for tetraphenylborate. Manometric measurement of CO released on addition of excess triphenylphosphine indicated the presence of two moles of CO per mole of catalyst.

The cationic moiety of the product is represented in FIG. 1.

EXAMPLE 2

Ligand: 1,4,7,11,14,17-hexaazaeicosane

The yield of the invention catalyst, isolated as the colorless bis-tetraphenylborate complex, was 59% when using 66.5 mg (0.349 mmole) CuI, 50 mg (0.175 mmole) ligand, and 119 mg (0.349 mmole) sodium tetraphenylborate.

Analysis calculated for $C_{64}H_{74}N_6O_2B_2Cu_2$: C, 69.36; H, 6.73; N, 7.58. Found: C, 68.83; H, 6.51; N, 7.47%. Characteristic IR absorption bands were observed at 3305 (m) and 3245 (m) for ligand NH; 2085 (s) for CO; and 740 (S) and 715 (S) $cm^{-1}$ for tetraphenylborate. Manometric measurement of CO released on addition of triphenylphosphine indicated the presence of two moles of CO per mole of catalyst.

EXAMPLE 3

Catalyzed Oxidation of Phenol to o-Benzoquinone

Phenol (2.2 mmole) was added to a solution under nitrogen of triethylamine (4.4 mmole) in $CH_2Cl_2$ (50 ml) containing suspended therein $CaSO_4$ anhyd.(1.5 g). Catalyst of FIG. 1 wherein a=w=5 as the tetraphenylborate (0.02 mmole) was added and excess oxygen was bubbled through the solution. After 24 hrs. at room temperature, the solvent was evaporated under reduced pressure. The residue was taken up in ether, filtered, and the ether was evaporated. The residue was analyzed by thin layer chromatrography (TLC) (silica gel), visible spectroscopy, $^1H$ nuclear magnetic resonance (nmr), and high performance liquid chromatography (HPLC) and found to contain:

20 (wt)% o-benzoquinone
20 (wt)% catechol
40 (wt)% unreacted phenol
20 (wt)% unidentified

EXAMPLE 4

The experiment of Example 3 was repeated using the tetraphenylborate catalyst of FIG. 1 wherein a=w=3 with the following results:

30 (wt)% o-benzoquinone
30 (wt)% catechol
20 (wt)% unreacted phenol
20 (wt)% unidentified No p-diphenols or p-quinones could be detected by TLC nor HPLC and no ring cleavage products such as muconic acid could be detected by infrared spectroscopy in the products of either Example 3 or 4. The unidentified fraction, probably related to o-quinone which is known to be highly reactive, appears to form after workup after the invention reaction.

That which is claimed is:

1. The process of molecular oxygen oxidation of a phenol having a phenolic hydroxyl group, at a position ortho to said phenolic hydroxyl group to produce product selected from the group consisting of o-quinones and catechols, said process being carried out in the presence of oxygen and an amount of catalyst effective to catalyze said oxidation, said catalyst having two proximate cations of Cu(I), each cation coordinated within a chelating center derived from ethylenediamine, diethylenetriamine, propylenediamine, or dipropylenetriamine, said centers being joined by two bridges selected from the group consisting of $-CH_2CH_2OCH_2CH_2-$ and alkylene radicals containing 2 to 5 carbon atoms in the main chain, said bridges connecting terminal nitrogen atoms of said amines whereby to form a macrocycle ligand having said chelating centers, with the proviso that when at least one of the chelating centers is derived from ethylenediamine, alkylene radicals, contain at least 4 carbon atoms in the main chain.

2. The process of claim 1 wherein at least one of the bridges is a branched alkylene radical.

3. The process of claim 1 wherein the macrocycle ligand is given by the formula:

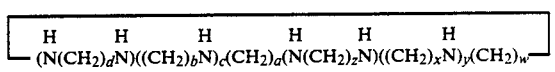

wherein:
a=2-5
b=2 or 3
c=0 or 1
d=2 or 3
w=2-5
x=2 or 3
y=0 or 1
z=2 or 3.

4. The process of claim 3 wherein: